US007828738B2

(12) United States Patent
Freiburger

(10) Patent No.: US 7,828,738 B2
(45) Date of Patent: Nov. 9, 2010

(54) STEERED CONTINUOUS WAVE DOPPLER METHODS AND SYSTEMS FOR TWO-DIMENSIONAL ULTRASOUND TRANSDUCER ARRAYS

(75) Inventor: Paul Donald Freiburger, Seattle, WA (US)

(73) Assignee: Siemens Medical Solutions USA, Inc., Malvern, PA (US)

( * ) Notice: Subject to any disclaimer, the term of this patent is extended or adjusted under 35 U.S.C. 154(b) by 601 days.

(21) Appl. No.: 11/904,909

(22) Filed: Sep. 28, 2007

(65) Prior Publication Data
US 2008/0027323 A1 Jan. 31, 2008

Related U.S. Application Data

(62) Division of application No. 10/787,695, filed on Feb. 26, 2004, now Pat. No. 7,637,871.

(51) Int. Cl.
*A61B 8/00* (2006.01)
(52) U.S. Cl. ............... 600/459; 600/455; 600/457
(58) Field of Classification Search ........ 600/453, 600/455, 457, 459, 447; 73/593; 367/119–123
See application file for complete search history.

(56) References Cited

U.S. PATENT DOCUMENTS

| H1171 H | 4/1993 | Fillhart |
| 5,267,221 A | 11/1993 | Miller et al. |
| 5,348,014 A | 9/1994 | Okado |
| 5,406,949 A * | 4/1995 | Yao et al. ............ 600/457 |
| 5,522,393 A | 6/1996 | Phillips et al. |

(Continued)

FOREIGN PATENT DOCUMENTS

CN    1342442 A    4/2002

(Continued)

OTHER PUBLICATIONS

Office Action, dated Oct. 5, 2007, for US 2005-0148873 A1 (U.S. Appl. No. 10/741,538).

(Continued)

*Primary Examiner*—Brian Casler
*Assistant Examiner*—Parikha S Mehta

(57) ABSTRACT

Methods and systems for acquiring spectral and velocity information with a multi-dimensional array are provided. For example, a dedicated receive aperture is formed at a multi-dimensional array for steered continuous wave imaging. Other elements not within the dedicated receive aperture are used for transmitting continuous waves or transmitting and receiving pulsed waveforms in other modes of imaging. As another example, switches or other structures are provided for selecting between a plurality of possible apertures for a steered continuous wave aperture. The selection is performed in response to a configuration of an ultrasound system, such as selection of a focal location or steer direction. The aperture is then used for either transmit or receive operations of steered continuous wave imaging. As yet another example, at least part of the steered continuous wave beamformer is provided within a transducer assembly. The transducer assembly includes a probe housing and a connector housing electrically connected by a cable. In yet another example, at least one angle of a three-dimensional indication of flow direction is input from a user. Velocity values in either steered continuous wave imaging or pulsed wave imaging are corrected as a function of a three-dimensional indication of flow direction.

6 Claims, 2 Drawing Sheets

U.S. PATENT DOCUMENTS

| | | | |
|---|---|---|---|
| 5,538,004 A | 7/1996 | Bamber | |
| 5,555,534 A | 9/1996 | Maslak et al. | |
| 5,562,097 A * | 10/1996 | Yao | 600/457 |
| 5,573,001 A | 11/1996 | Petrofsky et al. | |
| 5,590,658 A | 1/1997 | Chiang et al. | |
| 5,617,866 A | 4/1997 | Marian | |
| 5,622,177 A | 4/1997 | Breimeser et al. | |
| 5,627,536 A | 5/1997 | Ramirez | |
| 5,676,147 A | 10/1997 | Petrofsky et al. | |
| 5,678,551 A | 10/1997 | Stevens | |
| 5,690,114 A | 11/1997 | Chiang et al. | |
| 5,817,024 A | 10/1998 | Ogle et al. | |
| 5,820,549 A | 10/1998 | Marian | |
| 5,839,442 A | 11/1998 | Chiang et al. | |
| 5,957,846 A | 9/1999 | Chiang et al. | |
| 5,964,709 A | 10/1999 | Chiang et al. | |
| 5,997,479 A | 12/1999 | Savord et al. | |
| 6,013,032 A | 1/2000 | Savord | |
| 6,016,285 A | 1/2000 | Wright et al. | |
| 6,029,116 A | 2/2000 | Wright et al. | |
| 6,102,863 A | 8/2000 | Pflugrath et al. | |
| 6,106,472 A | 8/2000 | Chiang et al. | |
| 6,126,602 A | 10/2000 | Savord et al. | |
| 6,126,606 A | 10/2000 | Bergstoel | |
| 6,142,946 A | 11/2000 | Hwang et al. | |
| 6,248,073 B1 | 6/2001 | Gilbert et al. | |
| 6,371,918 B1 | 4/2002 | Bunce | |
| 6,375,617 B1 | 4/2002 | Fraser | |
| 6,491,634 B1 | 12/2002 | Leavitt et al. | |
| 6,527,722 B1 | 3/2003 | Fazioli et al. | |
| 6,530,887 B1 | 3/2003 | Gilbert et al. | |
| 6,540,685 B1 | 4/2003 | Rhoads et al. | |
| 6,544,175 B1 | 4/2003 | Newman | |
| 6,575,908 B2 | 6/2003 | Barnes et al. | |
| 6,582,367 B1 | 6/2003 | Robinson et al. | |
| 6,589,179 B2 | 7/2003 | Criton et al. | |
| 6,612,987 B2 | 9/2003 | Morsy et al. | |
| 6,629,928 B1 | 10/2003 | Dolan et al. | |
| 6,635,019 B2 | 10/2003 | Davidsen | |
| 6,648,826 B2 | 11/2003 | Little et al. | |
| 6,814,701 B1 | 11/2004 | Tamura | |
| 6,875,178 B2 | 4/2005 | Phelps et al. | |
| 6,932,517 B2 | 8/2005 | Swayze et al. | |
| 7,115,093 B2 | 10/2006 | Halmann et al. | |
| 7,169,108 B2 | 1/2007 | Little et al. | |
| 7,371,218 B2 | 5/2008 | Walston et al. | |
| 2003/0139664 A1 | 7/2003 | Hunt et al. | |
| 2004/0109028 A1 | 6/2004 | Stern et al. | |
| 2004/0181154 A1 | 9/2004 | Peterson et al. | |
| 2005/0148873 A1 | 7/2005 | Petersen et al. | |
| 2005/0148878 A1 | 7/2005 | Phelps et al. | |
| 2005/0192499 A1 | 9/2005 | Lazenby et al. | |
| 2005/0203391 A1 | 9/2005 | Phelps et al. | |
| 2005/0203404 A1 | 9/2005 | Freiburger | |
| 2008/0027322 A1 | 1/2008 | Freiburger | |

FOREIGN PATENT DOCUMENTS

| | | |
|---|---|---|
| EP | 1049407 B1 | 12/2005 |
| WO | WO 00/30540 | 6/2000 |

OTHER PUBLICATIONS

"Fully Sampled Matrix Transducer for Real Time 3D Ultrasonic Imaging," by Bernard Savord, Rod Solomon—Philips Medical Systems, 300 Minuteman Rd., Andover MA; 9 pgs.; before Dec. 2003.

* cited by examiner

STEERED CONTINUOUS WAVE DOPPLER METHODS AND SYSTEMS FOR TWO-DIMENSIONAL ULTRASOUND TRANSDUCER ARRAYS

CROSS-REFERENCE TO RELATED APPLICATION

This application is a divisional of U.S. patent application Ser. No. 10/787,695, filed Feb. 26, 2004, now U.S. Pat. No. 7,637,871.

BACKGROUND

The present invention relates to steered continuous wave Doppler ultrasound imaging.

Steered continuous wave Doppler imaging is provided using one-dimensional arrays. Dedicated transmit and receive apertures are used on the array, so coaxial cables and associated elements may be electrically isolated to avoid interference. The steered continuous wave Doppler receive beamformer is typically analog to provide large dynamic range and sensitivity. The data output by the steered continuous wave receive beamformer is used to generate a spectral Doppler image. A graph of velocities as a function of time is generated. For each given time, a range of velocities are highlighted. The highlighted velocities are modulated as a function of the associated energy. The range of velocities and associated energies at a given steer direction is displayed as a function of time as a moving graph.

The velocity information represents velocities towards and away from the transducer. Where blood flow is at an angle to the scan line, the actual velocity may differ. Various techniques are provided for angle correcting velocity information for two-dimensional imaging. For example, the user inputs an indication of the direction of flow within a two-dimensional image. The angle information is used to determine an actual velocity. As another example, the ultrasound system automatically acquires data at each spatial location from different angles and uses the angles and associated velocities to determine an actual velocity values. The angle information is used to determine an actual velocity. For two-dimensional imaging, the angle is applied to velocities at a plurality of locations in an image representing a scan region at a given time.

However, techniques applicable to one-dimensional arrays and two-dimensional imaging may not apply to steered continuous wave imaging using a two-dimensional array capable of three-dimensional imaging. Two dimensional arrays typically include hundreds or thousands of elements, such as an order of magnitude of 10 or more than one-dimensional arrays. Providing sufficient dynamic range and avoiding cross-talk may increase complexity and cost. Since circuitry may be provided within a transducer probe for each of the elements, the cost of providing sufficient dynamic range is increased for steered continuous wave imaging as compared to Doppler imaging using pulse waves.

BRIEF SUMMARY

By way of introduction, the preferred embodiments described below include methods and systems for acquiring spectral or velocity information with a multi-dimensional array. Various aspects are provided for overcoming hardware size, channel count and steering difficulties. For example, a dedicated receive aperture is formed on a multi-dimensional array for steered continuous wave imaging. Other elements not within the dedicated receive aperture are used for transmitting continuous waves or transmitting and receiving pulsed waveforms in other modes of imaging. To allow for steering throughout a volume, the dedicated receive aperture or a selected receive aperture may be symmetric about the center of the array. As another example aspect, switches or other structures are provided for selecting between a plurality of possible apertures for a steered continuous wave aperture. The selection is performed in response to a configuration of an ultrasound system, such as selection of a steer direction or an optimal focus location. The aperture is then used for either transmit or receive operations of steered continuous wave imaging. As yet another example aspect, at least part of the steered continuous wave beamformer is provided within a transducer assembly. The transducer assembly includes a probe housing and a releasable connector housing electrically connected by a cable. In yet another example aspect, at least one angle of a three-dimensional indication of flow direction is input from a user. Velocity values in either steered continuous wave imaging or pulsed wave imaging are corrected as a function of a three-dimensional indication of flow direction.

The present invention is defined by the following claims, and nothing in this section should be taken as limitation on those claims. Any of the various aspects or advantages discussed herein may be used independently or in any possible combination. In some embodiments, none of the aspects or advantages discussed herein may be provided. Further aspects and advantages of the invention are described below in conjunction with the preferred embodiments.

BRIEF DESCRIPTION OF THE DRAWINGS

The components in the figures are not necessarily to scale, emphasis instead being placed upon illustrating the principles of the invention. Moreover, in the figures, like reference numerals designate corresponding parts throughout the different views.

DETAILED DESCRIPTION OF THE DRAWINGS AND PRESENTLY PREFERRED EMBODIMENTS

To limit receive beamformer costs and electrical crosstalk, one embodiment uses dedicated receive channels for steered continuous wave imaging. Other channels are provided for transmit and receive operations in other modes on a multidimensional array. Dedicated channels form a subaperture that is symmetric about the center of the array, but non-symmetric subapertures may be used. In other embodiments, selectable receive or transmit apertures for steered continuous wave imaging are provided for a more uniform two-way response through rotation of the apertures as a function of the selected steering angle. The rotated apertures may be symmetric for further improved response. Angle correction is provided in response to user input for determining actual velocity values used for steered continuous wave or pulse wave imaging in yet other embodiments.

Figure 1:
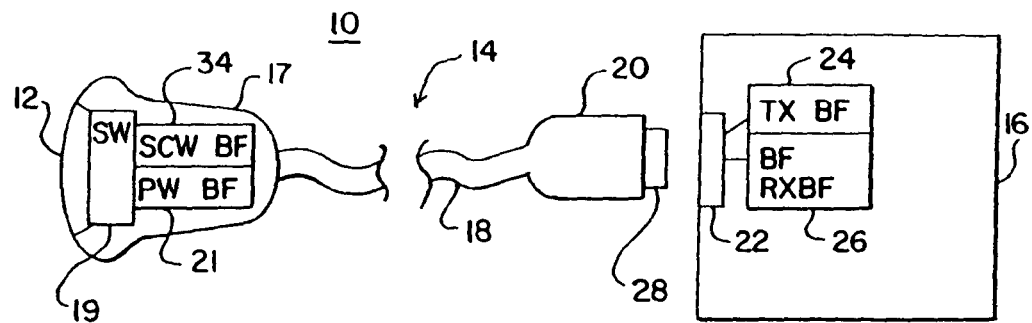
FIG. 1 is a block diagram of one embodiment of a system for acquiring spectral information with a multidimensional array.

FIG. 1 shows a system 10 for acquiring spectral information with a multidimensional transducer array 12. The system 10 is used to implement one or more of the above described dedicated receive aperture, selectable aperture and/or three-dimensional angle correction. The system 10 includes a transducer assembly 14 and an imaging system 16. In one embodiment, the transducer assembly 14 is detachable or releasably connectable with the imaging system 16. In other embodiments, the transducer assembly 14 is permanently attached to the imaging system 16. The system 10 is a cart-mounted, handheld, portable or other now known or later developed medical diagnostic ultrasound imaging system. Two example embodiments of the system 10 are disclosed in U.S. patent application Ser. Nos. 10/741,827 and 10/741,538, the disclosures of which are incorporated herein by reference.

The imaging system 16 is a medical diagnostic ultrasound imaging system in one embodiment. In other embodiments, the imaging system 16 is a computer, workstation or other medical imaging system. For an ultrasound system, the imaging system 16 includes a transmit beamformer 24 and a receive beamformer 26 connected with a connector 22. The transmit beamformer 24 is operable to generate a plurality of relatively delayed and apodized steered continuous or pulsed waveforms for transmitting acoustic energy. The electrical signals generated by the transmit beamformer 24 are routed to the connector 22. The connector 22 also electrically connects to the receive beamformer 26. In one embodiment, the connections within the imaging system 16 from the connector 22 are permanent and made through one or more switches, such as a transmit and receive switch.

The receive beamformer 26 is an analog or digital receive beamformer. The receive beamformer 26 includes a plurality of delays, amplifiers and one or more summers. The receive beamformer 26 is configured to receive analog signals, but may be configured to receive digital signals. The electrical signals representing different elements or groups of elements are relatively delayed, apodized and then summed to form samples or signals representing one or different spatial locations along one or more receive beams. The receive beamformer 26 is configured to provide a wideband interface, such as a switching matrix with 384-wire impedance controlled paths from the connector 22 to the beamforming cards or slots on the printed circuit board interconnects. Other switching matrix and number of paths may be provided.

In one embodiment, the receive beamformer 26 includes separate beamformers for either analog or digital data or as a function of imaging mode, such as a separate spectral Doppler beamformer and a separate B-mode and color-flow mode beamformer. For example, the receive beamformer 26 is a digital processor on a card, ASIC or other device, and a separate analog processor for continuous wave signals is provided on a separate card. One receive beamformer 26 may be used for both continuous and pulsed waveform beamformation.

The receive beamformer 26 may be distributed, such as different parts of the beamformer in different locations within the imaging system 16 or external to the imaging system 16 (e.g., a portion of the receive beamformer 26 within the transducer probe assembly 14). The steered continuous wave receive beamformer 26 may be at least partly in the transducer assembly 14 as designated by 34. For example, the steered continuous wave beamformer 34 includes a pre-amplifier, a delay or phase rotator, a summer or combinations thereof in a probe housing 17 of the transducer assembly 14. Alternatively, the steered continuous wave beamformer 26 is entirely in the transducer assembly 14 or the imaging system 16.

The components of the steered continuous wave receive beamformer 26, 34 have a dynamic range for continuous wave imaging, such as providing a type of preamplifier, sufficient power supply and minimal noise components for continuous wave imaging. The delays may be implemented with a single wavelength delay or phase capability. For comparison, the components for a pulsed wave or multi-dimensional imaging receive beamformer have multiple cycle delays with a higher resolution of delay and have a lesser dynamic range. In one embodiment, one or more of the components of the steered continuous wave beamformer 34, 26 and a pulsed wave beamformer are shared, such as preamplifiers, delays, amplifiers, summers or the entire receive channel path.

Further processes and associated circuitry are implemented by the imaging system 16 for generating an image or for calculating measurements from the receive beamformed information. Different, additional or fewer transmit and receive circuit devices or components may be provided.

The connector 22 is one of any now-known or later-developed mechanical and electrical connectors for detachably connecting and removing the transducer probe assembly 12. The connector 22 includes grooves, extensions, latches, screws, threaded holes or any other now-known or later-developed mechanical structure for releasably connecting to another device. A plurality of male or female electrical connections for connecting with individual digital traces, such as in a circuit board configuration, or for connecting with coaxial cables is provided. For example, 192 or other number of electrical connections of exposed metallic traces on a circuit board for mating are recessed within the connector 22. In one embodiment, the connector disclosed in U.S. Pat. No. 6,371,918, the disclosure of which is incorporated herein by reference, is used. While one connector 22 is shown, a plurality of different connectors may be provided for connecting to a same type or different types of transducer probe assemblies 12. The connector 22 electrically connects with the receive beamformer 26 for communicating analog or digital signals. In alternative embodiments, the connector 22 is a standard or custom connection on a PC, digital repeater or other electrical device for locally processing data or for transmitting data for remote processing.

The ultrasound transducer probe assembly 14 includes the transducer probe housing 17, a cable 18, and a connector housing 20. Additional, different or fewer components may be provided. For example, a hand-held system 10 is provided where the transducer probe housing 17 is included as part of the connector housing 20 without the cable 18. The transducer probe assembly 14 provides a detachable transducer.

The transducer probe housing 17 is plastic, metal, rubber, combinations thereof or any other now-known or later-developed material for housing a multidimensional transducer array 12 of elements. In one embodiment, the transducer probe housing 17 is shaped for hand-held use. In other embodiments, the transducer probe housing 17 is shaped for use internal to a patient, such as shaped as an endoscope or catheter. The transducer probe housing 17 at least partially houses the multidimensional array 12 of elements, such as covering a portion of the array 12 and allowing a face of the array 12 acoustical access for scanning a patient.

The elements of the array 12 are piezoelectric, capacitive membrane ultrasound transducer or other now-known or later-developed elements for converting between electrical and acoustical energies. The multidimensional array 12 is distributed in any of various patterns, including triangular, square, rectangular, hexagonal or other now known or latter developed grids. Full or sparse sampling of the elements within the grid is used. For example, a 2-dimensional array has 1,920 or other number of fully-sampled elements in a square, hexagonal, triangular or rectangular grid positioned on a planar or curved surface. The transducer array 12 includes a flex circuit, signal traces or other structures for electrical interconnection from the elements of the array 12 to other electronics of the probe assembly 12. For example, the flex circuits are connected to a plurality of coaxial cables in the cable 18 or to electronics or connector within the connector housing 20.

In an alternative embodiment, the transducer array 12 electrically connects to electrical components within the probe housing 17, such as switches 19, the steered continuous wave beamformer 34 and/or the pulsed wave beamformer 21. For example, the switches 19 are a transistor network, cross-point network or multiplexer electrically connected between the plurality of cables of the cable 18 and the transducer elements of the array 12. The switches 19 are positioned in the transducer probe housing 17 with the array 12. The switches 19 are operable to selectably connect different elements to different receive beamformer channels. Where a selectable transmit, receive or both transmit and receive aperture for steered continuous wave beamforming is used, the switches 19 allow connection of different elements to different transmit and receive channels for defining the apertures. Multi-layer or single layer switching may be used for routing signals from each element to a selected one or more channels. The switches 19 may allow connection to any one or more of a sub-set or all of the transmit and/or receive channels.

In one embodiment, the switches 19 are provided for a sub-set of the elements. Other elements are permanently connected as a dedicated receive aperture for use with steered continuous waveforms. The non-dedicated elements are used for transmit steered continuous waveform operation and transmit and receive operation in other modes of imaging, such as pulsed wave imaging (e.g., two or three dimensional B-mode or color mode imaging). In alternative embodiments, a dedicated receive aperture for steered continuous wave imaging includes switches for selecting different ones of the elements for connection with different channels of the steered continuous waveform beamformer 34, 26. In yet other embodiments, the switches 19 are used for the entire array without a dedicated steered continuous wave aperture, such as for using selectable steered continuous wave apertures.

In one embodiment, at least a portion of the steering continuous wave beamformer 34 is provided in the probe housing 17 or transducer assembly 14. For example, pre-amplifiers, delays, phase rotators amplifiers and summers are provided for partially beamforming a plurality of sub-apertures of a receive aperture. As another example, signals from elements associated with a same or similar delay are routed together (i.e., summed) using switches 19 to partially beamform the signals for a sub-aperture prior to or after applying the delay. The delays are either included within the transducer assembly 14 or the imaging system 16. Other components may also be included, such as filters. Fewer components of the steering continuous wave beamformer 34, 26 may be provided in the probe housing 17 or transducer assembly 14, such as components prior to delay, prior to amplification for apodization or prior to summation.

Other electronics may be provided in the probe housing 17 or the connector housing 20. For example, electronics operable to multiplex signals from a plurality of elements onto a fewer number of outputs using time division multiplexing. In alternative embodiments, other forms of multiplexing are provided. Preamplifiers or other structures are also included in other embodiments with the multiplexer. For example, the structures disclosed in U.S. Pat. Nos. 6,875,178 and 7,371,218, the disclosures of which are incorporated herein by reference, are used. For a multidimensional array, signals from every 2, 4, 8 or other number of elements are multiplexed onto a common output. A plurality of outputs for different groups of elements is provided. In alternative embodiments, the probe electronics are different components for the same or different functions, or the transducer probe housing 17 is provided without the further electronics. In another embodiment, the probe electronics include delays, amplifiers and summers for performing beamforming functions for sub-arrays or across the entire array.

The cable 18 includes a plurality of coaxial cables. For example, 64, 128, 192 or other number of coaxial cables are provided for transmitting electrical signals representing acoustic energy received at elements of the array 12. Each coaxial cable receives information for one element, information from a sub-array or multiplexed information representing a plurality of different elements. In alternative embodiments, the cable 18 is a flexible circuit, optical data path, fiber optic, insulated wires or other now-known or later-developed structure. For example, analog-to-digital converters are provided in the transducer probe housing 17, and digital signals are transmitted along now-known or later-developed digital paths through the cable 18. The cable 18 electrically connects the ultrasound transducer array 12 to the electronics of the connector housing 20 or imaging system 16. Where multiplexing or partial beamforming is provided, fewer cables than elements may be used. In the embodiment with a dedicated steered continuous wave receive aperture, the cables associated with the dedicated aperture may be shielded from other cables to reduce any cross-talk. The shielding is in addition to the coaxial shielding, such as a sheet of dielectric material separating dedicated receive cables from other cables. In other embodiments, such as the selectable aperture embodiments, the shielding between cables is provided by the coaxial or other shielding resulting from the cables being used.

The connector housing 20 is metal, plastic, rubber, combinations thereof or other now-known or later-developed material for housing or at least partially housing a releasable connector 28 and any other optional components. The connector housing 20 is connected at the end of the cable 18, so that the connector housing 20 is spaced from the ultrasound transducer array 12 and associated probe housing 17.

The connector housing 20 is shaped to allow detachment and attachment to the imaging system 16. In one embodiment, now-known connector housings are extended in length away from the connector 28 to accommodate the additional electronics, such as extending by twice the distance used for connectors without electronics to accommodate demultiplexers, partial beamformers, analog-to-digital converters or other components. Different changes in dimension may be provided, such as making the connector housing 20 longer, higher, wider or combinations thereof.

The releasable connector 28 electrically connects with the ultrasound transducer array 12 without any detachable connections. Alternatively, one or more detachable connections are provided, such as at the interface between the cable 18 and the probe housing 17. The connector 28 is releasably connectable with the imaging system 16. The connector 28 includes mechanical and electrical structures corresponding to the mechanical and electrical structures of the connector 22 of the imaging system 16. For example, a plurality of electrical signal lines for connection with exposed traces on a circuit board protrudes from the connector housing 20 for insertion into the connector 22. The connectors 22, 28 include power, clock, synchronization or other control lines for implementing the digital processing within the connector housing 20 or the transducer probe assembly 12 in synchronization with a format usable by the imaging system 16. Latches, extensions, screws, threaded holes or other now-known or later-developed releasable connection structures are provided for mechanically attaching the connectors 28 and 22. In one embodiment, the connector 28 is a connector as disclosed in U.S. Pat. No. 6,371,918. Different connectors may be provided. The connector 28 and 22 are operable to easily detach and attach. Through rotation, latching or other processes, the connectors 22, 28 are attached or detached in seconds or tens of seconds. Longer time periods may be used for more solid connections or for different connectors.

Figure 2:
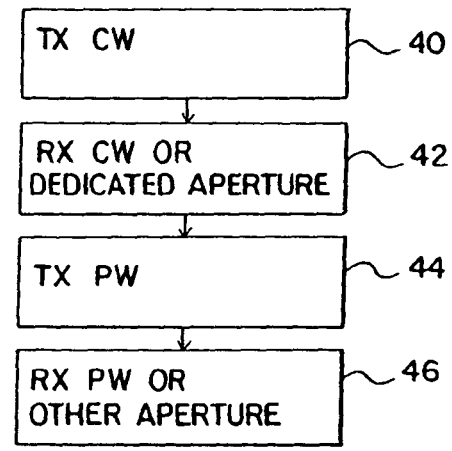
FIG. 2 is a flow chart of one embodiment of a method for using a dedicated receive continuous wave aperture on a multidimensional array.

FIG. 2 shows one embodiment of a method for acquiring spectral information with a multidimensional transducer array. A multidimensional transducer array is used in the system 10 as described above for FIG. 1 or a different system. Additional, different or fewer acts than shown in FIG. 2 may be used, such as providing for the transmission and reception of continuous waves in acts 40 and 42 independent of or without the pulsed wave transmission and reception of acts 24 and 46.

In act 40, continuous waves are transmitted from the multidimensional array. The continuous waves include waveforms with a plurality of cycles, such as about 10, tens or hundreds of cycles. While the term "continuous" is used, the waveforms have a beginning and an ending to allow interleaving or discreet uses of the continuous wave imaging. For steered continuous wave imaging, continuous waves are transmitted from a plurality of different elements with relative delays or phasing and apodization. The delays and apodization are selected to focus the continuous waveforms at a desired location, such as a user selected focal position.

In act 42, echoes responsive to the transmitted continuous waves are received on a dedicated aperture of a multidimensional transducer array. The receive aperture is dedicated to receiving steered continuous waveform echoes, such as being switchably or permanently connected to a receive beamformer for steered continuous wave beamforming. The remainder of the array is used for the transmission of steered continuous waveforms and transmission and reception in other imaging modes. For example, a portion or the entirety of the remainder of the multidimensional array not dedicated to receiving steered continuous waveforms, is used for performing B-mode and/or multidimensional Doppler imaging. The subaperture used for continuous wave transmission and other imaging modes uses the common hardware, cables or circuitry provided with the multidimensional array. The elements and associated cables or other signal paths of the dedicated subaperture used for receiving continuous wave signals is independently shielded from other channels. Where the continuous wave receive beamformer is provided within the imaging system, the signal paths from the multidimensional transducer array to the receive beamformer are also dedicated. For either local or remote receive beamforming, the receive beamformer channels for the dedicated aperture provide sufficient or optimized dynamic range and sensitivity. Channels connected to other portions of the multidimensional transducer array may have reduced size and complexity for other imaging modes or transmission of steered continuous waves.

In one embodiment, the elements of the dedicated receive aperture have a larger pitch than elements of the multidimensional array of a different subaperture. For example, the multidimensional transducer array is manufactured with different sized PZT posts or kerfing profiles to provide a larger pitch for the dedicated receive aperture. The large pitch may reduce the number of steered continuous wave receive beamformer channels and associated cables communicating information back to an imaging system. As another example, adjacent or elements spaced apart within the dedicated receive aperture are switchably shorted together, such as where the elements are associated with a same or similar delay or phase shift given a selected steering angle. By shorting together adjacent or spaced apart elements, a larger pitch is provided than where elements are not shorted together. The effects of grating lobes may be minimized by using a fully sampled transmit aperture. In alternative embodiments, a same pitch is provided in both the dedicated steered continuous wave receive aperture as well as the other subaperture used for transmit or other imaging modes.

Figure 3:
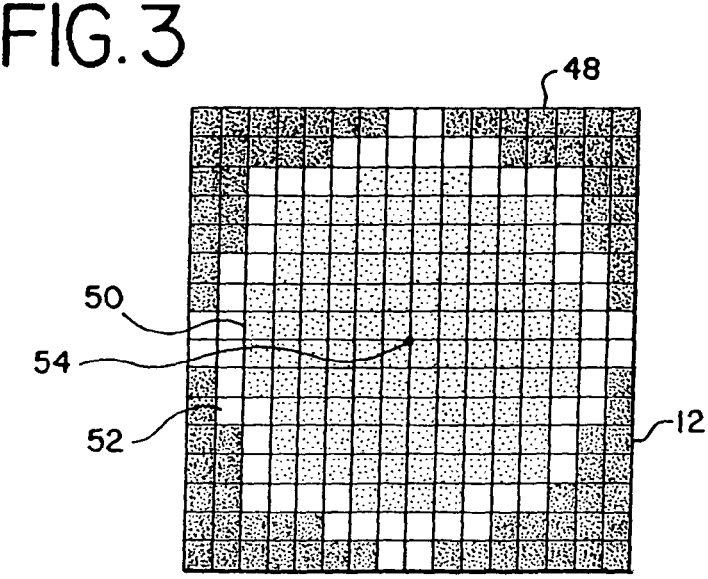
FIG. 3 is a graphical representation of one embodiment of a symmetrical dedicated receive aperture for continuous waving imaging with a multidimensional array.

The dedicated receive aperture is positioned in any of various continuous or sparse positions within the multidimensional transducer array. In one embodiment, the dedicated receive aperture is symmetric about a center of the multidimensional transducer array. FIG. 3 shows one embodiment of a dedicated receive aperture symmetric about the center of the multidimensional transducer array 12. The array 12 is a 16×16 array of elements in a fully sampled square grid, but other samplings and grid distributions may be provided. The elements of the dedicated receive aperture 48 are positioned at the corners of the array 12. For example, an equal number of elements in a same distribution are provided at each of the corners for the dedicated receive aperture 48. Each of the elements within the dedicated receive aperture operates independently or connects to a separate receive beamformer channel, but one or more of the elements may be shorted together as a function of the steering direction or other reason. The dedicated receive aperture 48 is symmetric along both dimensions of the multidimensional transducer array 12 about the center 54. By providing a symmetric dedicated receive aperture, the effects of steering away from the receive aperture are minimized. The remaining elements of the array 12 used for transmit operation or transmit and receive operations in other imaging modes. For steered continuous wave operation, an optional buffer 52 of one or more elements between the elements of the dedicated receive aperture 48 and the elements of a transmit aperture 50 are shown in FIG. 3 between the receive aperture 48 and a transmit aperture 50. The buffer 52 minimizes crosstalk between transmit and receive elements. In alternative embodiments, the buffer elements 52 are not provided or a wider buffer is provided.

For operation in other imaging modes, the elements of the subaperture 50 and/or buffer aperture 52 are used for both transmit and receive operation. For other modes of operation, such as B-mode, the corner or edge elements contribute less to the resulting image, so dedication of the elements to a steered continuous wave receive aperture may have minimal effects. A tradeoff between the size of the dedicated receive aperture, the associated sensitivity and imaging performance of other imaging modes using the remaining subaperture 50 of the array 12 is selected as a function of intended application or possible applications. A greater or lesser number or percentage of the array 12 may be used for the dedicated receive aperture. In other embodiments, a portion or all of the dedicated receive aperture is spaced from one or more of the edges of the array 12. A portion or the entirety of a continuous aperture region of the dedicated receive aperture may be positioned at the center 54 of the array 12 in yet other embodiments. Non-symmetric distributions may also be used.

In act 44, pulse waves are transmitted with elements of the multidimensional array that are separate from the elements of the dedicated receive aperture. For example, the same or an overlapping aperture used for transmission of the steering continuous waves is used for transmitting pulse waves. The pulse waves comprise one to four cycles, but a greater number of cycles may be provided in other embodiments. Pulse waves are used or configured for generating two- or three-dimensional image representations, such as transmitting along a plurality of different scan lines in sequence as part of a scan. In act 46, the same or a slightly different aperture is used to receive signals responsive to the transmitted pulse waves. For example, elements of the multidimensional transducer array other than the dedicated receive aperture are used for receiving the pulse wave echo signals.

By providing a dedicated receive aperture for steered continuous waveforms, various components of the receive aperture may be shielded from components associated with the remainder of the elements of the array. For example, preamplifiers, cables, receive beamformer circuits and combinations thereof within the transducer assembly 14 of the dedicated receive aperture are shielded from other devices. Amplifiers or receive beamformer circuits may be shielded by a physical shield structure or separation on different circuit boards or flexible circuits. Echo signals received in response to steered continuous waves are transmitted to a dedicated continuous wave beamformer over a path separate from signals received in response to transmitted pulsed waves or a path separate from transmit waveforms. The separation may minimize or reduce crosstalk and allow for shielding. Alternatively, the separate path is provided without the shielding.

Figure 4:
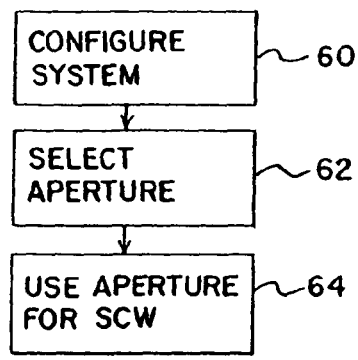
FIG. 4 is a flow chart diagram of one embodiment of a method for selecting apertures for continuous wave imaging.

FIG. 4 shows one embodiment of a method for acquiring spectral information with a multidimensional array. The method uses the system 10 or a different system. Additional, different or fewer acts may be provided in alternative embodiments. The method provides for a selectable transmit and/or receive apertures in a multidimensional array for steered continuous waveform imaging.

In act 60, the ultrasound system is configured for continuous wave operation. For example, the user selects a continuous wave imaging application. The system automatically configures the transmit and receive beamformers, and any other processors for acquiring spectral Doppler information. As another example, the user indicates a focus location or a steer direction within a multidimensional image, such as a color Doppler image, for acquiring spectral Doppler information. As a result of the selected focus position or steer direction, various transmit and receive beamformer parameters for steered continuous waves are established or selected from a table.

In act 62, an aperture is selected in response to the configuration. A plurality of possible apertures is available, such as two, three or more possible apertures. Each aperture corresponds to a different steering angle, different scan line origin, different depth or combinations thereof. In one embodiment, the selected aperture is a receive aperture. In other embodiments, the selected aperture is a transmit aperture.

Figure 5:
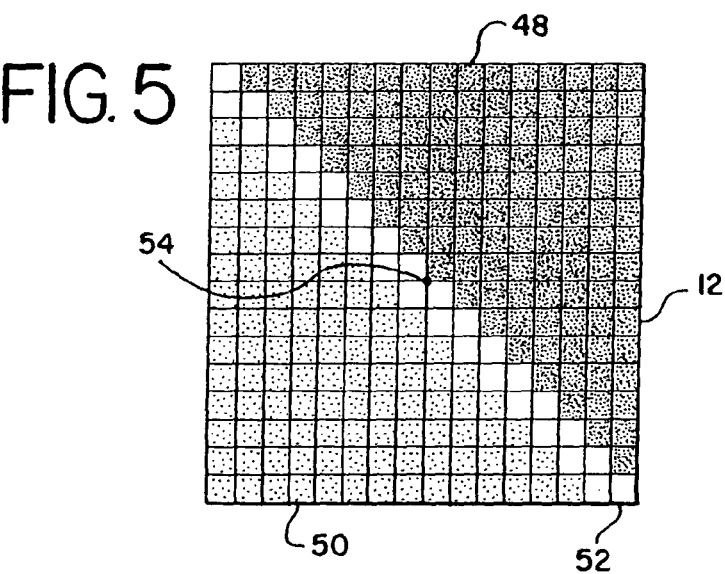
FIGS. 5 and 6 are graphical representations of different selected apertures on a multidimensional array.
Figure 6:
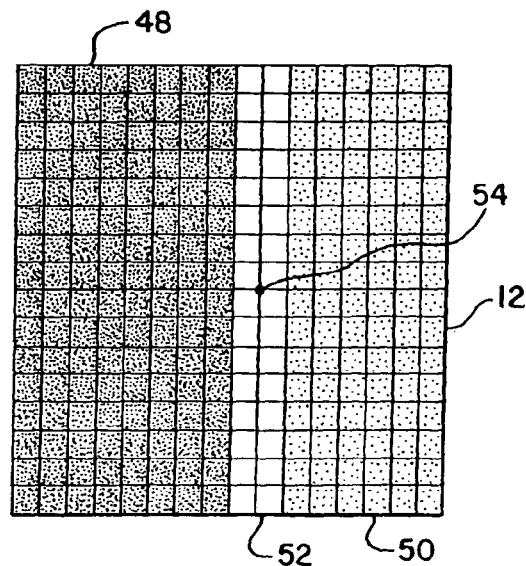

FIGS. 5 and 6 show two different aperture configurations for steered continuous wave imaging, representing rotation of an aperture as a function of scan line direction. For a given steer direction or focal location for spectral Doppler imaging, a fixed scan line and associated transmit and receive apertures are selected. Alternatively, the location of the focus or steer direction is tracked to account for tissue or transducer movement. As a result, the scan line and associated transmit and receive apertures may vary as a function of time. In either case, the aperture configuration of FIG. 5 is used for different origins, steering angles or depth than the aperture configuration of FIG. 6. As shown, a transmit aperture 50 on a multidimensional transducer array 12 is shown separated from a receive aperture 48 by a buffer of elements 52. The aperture configuration of FIG. 5 is shown rotated about the center 54 of the array 12. FIG. 5 is used for scan lines at an angle of about 45° clockwise on the face of the array 12. In alternative embodiments, the aperture configuration of FIG. 5 is used for scan line angles of about 135° to the face of the array 12. Alternatively, the transmit and receive apertures 48 and 50 are flipped about the buffer 52 for scan lines at about a 135° angle to the face of the transducer 12. FIG. 6 shows an aperture configuration for scan lines steered at an angle of 270° to the array 12 where 0° is straight up from the center 54 on the face of the array 12. The apertures of FIG. 5 and FIG. 6 may be used for other angles or for a range of possible angles. Different numbers of selectable aperture configurations may be provided for different range groupings of steering angles. While FIGS. 5 and 6 show rotation symmetrically about the center 54 of the array 12, asymmetric rotations may also be provided. By orienting the aperture configurations with the receive aperture closest to the focal point in an off-axis steered scan line, a more uniform two-way response may be provided. The voltage associated with transmit may be increased or decreased to account for the further distance of the transmit aperture from the focal region. While FIGS. 5 and 6 show contiguous transmit and receive apertures 50, 48, transmit or receive apertures 48, 50 with different shapes may be used. For example, the transmit and receive aperture configuration of FIG. 3 is selected in one embodiment, such as for a focal location orthogonal to the center 54 of the array 12 or in a range of angles around the orthogonal.

Other possible apertures include transmit or receive apertures 48, 50 with different sizes. For example, transmit or receive beamformer channels for steering continuous wave imaging may be limited, resulting in fewer elements within one of the transmit or receive apertures. Where such limitations exist, the other of the receive or transmit aperture may be increased or decreased in size to compensate for or correspond with the size of the other aperture. Where further off-axis steering is provided, the size of the apertures may be increased to compensate for sample volume increases. The greater aperture size may increase the amount of focus. For example, a smaller receive aperture may be selected. As a result, a larger transmit aperture is selected to provide a tight focus and better two-way response. The size and shape of the apertures may be selected a function of the depth of the focal point. As larger steering angles are used, larger transmit and/or receive apertures may be provided for the steered continuous wave operation.

The relative positions of the transmit and/or receive apertures on the array 12 may also be varied. The relative center of the transmit, receive or both apertures may be selected at different locations, such as sliding the apertures to different locations on the array 12. For example, the origin of the scan line extending through a selected focal location is shifted on the array. For example, the center of the transmit or receive aperture is shifted away from the center 54 of the array. The shift may make the scan line angle more orthogonal to the array 12. Alternatively, the shift avoids transmitting acoustic energy of the steered continuous waveforms through an undesired tissue boundary or other structure, such as bone.

In act 64, the selected aperture is used for steered continuous wave operation. For example, either transmit or receive operations are performed with the selected aperture. In one embodiment, both transmit and receive apertures are selected from a plurality of possible transmit and receive apertures, such as three or more of each. In an alternative embodiment, a dedicated or fixed receive aperture is used. The transmit aperture varies within the array 12 using elements other than elements dedicated to the receive aperture. For example, the transmit aperture 50 of FIG. 3 is increased in size or reduced in size as a function of the steering continuous wave configuration. The shape or relative position within available elements may also be selected.

Where a different steered continuous wave configuration is implemented, such as through user selection of a different focal range position, steer direction or through system automated selection of a different focal range position, the same or different transmit and/or receive apertures are selected for the new configuration. For example, different receive and transmit apertures are selected from at least two, three or more possible transmit and receive aperture configurations on a multi-dimensional array in response to a different steering angle.

Figure 7:
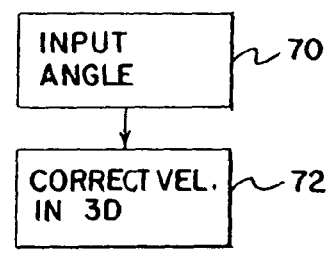
FIG. 7 is a flow chart diagram of one embodiment of a method for angle correcting velocity information using a multidimensional transducer array.

FIG. 7 shows one embodiment of a method for acquiring velocity information with a multidimensional array. The method of FIG. 7 uses the system 10 or a different system. Additional, different or fewer acts may be provided. The velocity values acquired for steered continuous wave or pulse wave imaging are corrected as a function of an angle of flow. Since multidimensional transducer arrays may be used for three-dimensional or real time four-dimensional imaging, the angle correction applied is for a three-dimensional indication of the flow direction.

In act 70, the user inputs at least one angle of a three-dimensional indication of flow direction. For example, a three-dimensional representation is generated as an image on a display. Through rotation or other three-dimensional imaging techniques, a beginning and end location of a three-dimensional vector within the represented three-dimensional space is selected by the user. The three-dimensional vector provides an angle relative to each of three axes for the vector. In an alternative embodiment, the user selects one or two angles of a three-dimensional vector. The system automatically determines other angles or an assumed angle is used. For example, the user rotates a three-dimensional representation until the vessel or flow of interest is at a desired angle on the screen, such as horizontal or vertical. In response to an input, such as a depression of a key, the three-dimensional vector is determined from a two-dimensional image representing three-dimensions on the screen. For example, a cross-sectional two-dimensional image of a three-dimensional scan volume is displayed for the user to select the three-dimensional vector. Automatic determination of one or more angles of the three-dimensional vector is performed using an analysis of flow data, different scan lines intersecting the same location or other now known or later developed techniques. For example, an automatic technique is used to determine flow along one or two-dimensions. The user then indicates a direction of flow along a third dimension. The three-dimensional indication of flow may be used for spectral Doppler, two-, three- or four-dimensional imaging.

The three-dimensional indication of the flow direction is provided at a single location in one embodiment. For steered continuous wave imaging, the single three-dimensional vector may be used. For two- or three-dimensional imaging, either a single or multiple user input three-dimensional indications of flow direction are provided. For example, the flow direction is assumed to be the same throughout a scanned volume. As another example, the flow direction indication is used for only a region of a volume, and different flow direction indicators are provided for different regions. In yet other embodiments, a system automatically determines the flow direction in three-dimensions for each of a plurality of spatial locations based on a flow direction indicated by the user at a single location or at multiple locations.

In act 72, the velocity values are corrected as a function of the three-dimensional indication of flow direction. Velocity values estimated using an ultrasound system correspond to velocities towards and away from the ultrasound transducer along a scan line. By determining the angle of the three-dimensional flow relative to the scan line position, the velocity values may be corrected. The magnitude of flow along the scan line in combination with the three-dimensional angle allows determination of the actual velocity at each location. For steered continuous wave imaging, the velocities of the spectral determination are corrected. As a result, the range of velocities and associated energies for a given range gate or focal location are determined as actual velocities. Alternatively, two- or three-dimensional Doppler velocities are corrected for each of a plurality of locations in a two- or three-dimensional representation.

While the invention has been described above by reference to various embodiments, it should be understood that many changes and modifications can be made without departing from the scope of the invention. It is therefore intended that the foregoing detailed description be regarded as illustrative rather than limiting, and that it be understood that it is the following claims, including all equivalents, that are intended to define the spirit and the scope of this invention.

I claim:

1. A method for acquiring spectral information with a multi-dimensional array, the method comprising:
   (a) transmitting continuous waves from the multi-dimensional array;
   (b) receiving signals responsive to (a) at a dedicated steered continuous wave receive aperture of the multi-dimensional array;
   (c) transmitting pulsed waves with elements comprising the multi-dimensional array separate from the elements comprising the dedicated steered continuous wave receive aperture; and
   (d) receiving signals responsive to (c) with elements comprising the multi-dimensional array separate from the elements comprising the dedicated steered continuous wave receive aperture.

2. The method of claim 1 wherein the dedicated steered continuous wave receive aperture is symmetric about a center of the multi-dimensional transducer array.

3. The method of claim 1 wherein the multi-dimensional transducer array comprises an array on one of a rectangular, triangular, hexagonal and square grid, the dedicated steered continuous wave receive aperture comprises elements in the outer corners of the multi-dimensional transducer array.

4. The method of claim 1 further comprising:
   (e) shielding at least one of: pre-amplifiers, cables, receive beamformer circuits and combinations thereof within a transducer probe assembly of the dedicated steered continuous wave receive aperture from other devices.

5. The method of claim 1 further comprising:
   (e) transmitting the signals received during (b) to a dedicated continuous wave beamformer over a path separate from signals received during (d).

6. The method of claim 1 wherein elements of the dedicated steered continuous wave receive aperture have a larger pitch than the elements of the multi-dimensional array separate from the elements of the dedicated steered continuous wave receive aperture.

* * * * *